(12) United States Patent
Von Bergen et al.

(10) Patent No.: US 12,109,422 B2
(45) Date of Patent: Oct. 8, 2024

(54) ELECTRICAL CONNECTOR AND COVER FOR SIMULTANEOUSLY CONNECTING WIRES, BEDSIDE MONITOR, AND TEMPORARY PACEMAKER

(71) Applicant: Wisconsin Alumni Research Foundation, Madison, WI (US)

(72) Inventors: Nicholas Von Bergen, Middleton, WI (US); Matthew Knoespel, Madison, WI (US); Philip Terrien, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 1227 days.

(21) Appl. No.: 16/786,433

(22) Filed: Feb. 10, 2020

(65) Prior Publication Data

US 2021/0244953 A1 Aug. 12, 2021

(51) Int. Cl.
*A61N 1/37* (2006.01)
*A61B 5/00* (2006.01)
(Continued)

(52) U.S. Cl.
CPC .......... *A61N 1/3752* (2013.01); *A61B 5/0006* (2013.01); *A61B 5/339* (2021.01);
(Continued)

(58) Field of Classification Search
CPC ...... A61N 1/3752; A61N 1/0587; A61N 1/36; A61N 1/3704; A61N 1/3625; A61N 1/0595; A61B 5/0006; A61B 5/339; A61B 5/686; A61B 5/02438; A61B 5/0245; A61B 5/273; H01R 13/5213; H01R 2201/12

See application file for complete search history.

(56) References Cited

U.S. PATENT DOCUMENTS 5,755,743 A * 5/1998 Volz ................... H01R 13/5219
607/36
2003/0040784 A1* 2/2003 Pasternak ............ A61N 1/3752
607/116

(Continued)

FOREIGN PATENT DOCUMENTS

| EP | 0339876 | 11/1989 |
|---|---|---|
| KR | 10-2009-0087729 | 8/2009 |
| WO | 2020112776 | 6/2020 |

OTHER PUBLICATIONS http://aemedical.com/products/pacing-wires/, A&E Medical Corporation.
(Continued)

*Primary Examiner* — Amanda K Hulbert
*Assistant Examiner* — Natasha Patel
(74) *Attorney, Agent, or Firm* — Boyle Fredrickson, S.C.

(57) ABSTRACT

An interface unit for epicardial pacemaking and telemetry monitoring connects a pacemaker and bedside monitor for simultaneous pacing during electrogram visualization using epicardial pacing leads. The interface unit provides an electrically insulating housing having single handed manual attachment of the epicardial leads and a retractable protective shroud extending over the epicardial leads. The interface unit further provides electrical connectors for selective attachment to the pacemaker and bedside monitor.

20 Claims, 10 Drawing Sheets

(51) Int. Cl.
  *A61B 5/339*  (2021.01)
  *A61N 1/05*   (2006.01)
  *A61N 1/36*   (2006.01)
  *A61N 1/375*  (2006.01)
  *H01R 13/52*  (2006.01)

(52) U.S. Cl.
  CPC ............ *A61B 5/686* (2013.01); *A61N 1/0587* (2013.01); *A61N 1/36* (2013.01); *A61N 1/3704* (2013.01); *H01R 13/5213* (2013.01); *H01R 2201/12* (2013.01)

(56) References Cited

U.S. PATENT DOCUMENTS

| | | | |
|---|---|---|---|
| 2007/0255156 A1* | 11/2007 | Mertz | A61B 5/283 |
| | | | 600/527 |
| 2008/0004535 A1* | 1/2008 | Smits | A61B 5/287 |
| | | | 600/509 |
| 2016/0166171 A1 | 6/2016 | Warner et al. | |
| 2018/0036542 A1* | 2/2018 | Von Bergen | A61B 5/30 |
| 2018/0221654 A1* | 8/2018 | Hess | A61N 1/3625 |
| 2019/0343414 A1 | 11/2019 | Drakulic et al. | |

OTHER PUBLICATIONS https://www.ugmedical.com/pdf/11LeadPtCable.pdf, A&E Medical Corporation.

\* cited by examiner

ELECTRICAL CONNECTOR AND COVER FOR SIMULTANEOUSLY CONNECTING WIRES, BEDSIDE MONITOR, AND TEMPORARY PACEMAKER

CROSS REFERENCE TO RELATED APPLICATIONS

--

STATEMENT REGARDING FEDERALLY SPONSORED RESEARCH OR DEVELOPMENT

--

BACKGROUND OF THE INVENTION

The present technology relates to an interface unit for epicardial pacemaking and telemetry monitoring, and more particularly, to an electrical connector for a pacemaker and bedside monitor providing for simultaneous pacing during electrogram visualization using epicardial pacing leads.

Telemetry monitoring allows medical professionals to monitor the electrical activity of the heart in real time and for extended periods of time. Telemetry monitoring is often used following cardiac surgery, when patients are most at risk for arrhythmias. Surface electrocardiographic (ECG) electrodes are traditionally placed on the patient's skin to detect and monitor the cardiac rhythms.

Due to the risk of postoperative arrhythmias, many patients have temporary pacing wires placed on the outside of their heart epicardium to permit pacing of the heart by a temporary, external pacemaker.

Traditionally, cardiac rhythms are obtained from surface ECG electrodes placed on the patient's chest and viewed on bedside monitors. However, atrial signals are not easily visualized using surface ECG electrodes. Therefore, when the medical professional detects an irregularity, the traditional solution is for an ECG technician to connect the epicardial pacing wires to an ECG monitor so that a medical professional can interpret the ECG signals with more accuracy. In other words, the epicardial pacing wires are positioned closer to the atrial impulses than any surface ECG electrode and therefore had high quality information in the atrial waveform. If an arrhythmia is detected and the medical professional wishes to pace the heart, the epicardial pacing wires then must be detached from the ECG monitor and reconnected to a temporary pacemaker for pacing.

The process of connecting and disconnecting the epicardial pacing wires is time-consuming and may need to be repeated for successive rounds of visualization and pacing. This also carries with it a risk of misconnection of three sets of connectors from the ECG monitor, the pacemaker, and the epicardial connections.

SUMMARY OF THE INVENTION

The present invention provides an interface unit for epicardial pacemaking and telemetry monitoring that simultaneously connects a pacemaker and bedside monitor for simultaneous pacing during electrogram visualization using epicardial pacing leads. The interface unit provides an electrically insulating housing having single handed manual attachment of the epicardial leads and a retractable protective shroud extending over the epicardial leads. The interface unit further provides electrical connectors for selective attachment to a pacemaker and bedside monitor.

The present invention provides, in one aspect, an interface unit for epicardial pacemaking and telemetry monitoring including an electrically insulating housing; a first and second electrical terminal accessible through corresponding apertures in the housing and adapted to releasably receive a first and second epicardial lead wires to an interior of the housing parallel to an insertion axis; a first electrical connector attached to the insulating housing to releasably receive a pacemaker connector at third and fourth electrical terminals; a second electrical connector attached to the insulating housing to receive a telemetry monitor connection at a fifth terminal; a circuit positioned within the housing, the circuit providing electrical communication between the second and third electrical terminals and between the first, fourth terminal and the fifth terminal; and an electrically insulating shroud providing a first and second aperture for receiving the first and second epicardial wire therethrough before the first and second epicardial wire is received by the first and second electrical terminal and movably attached to the housing to move between a first position proximate to the first and second terminal and a second position removed from the first and second terminal providing an insulating cover over the first and second epicardial wires extending outward from the first and second terminals.

It is thus a feature of at least one embodiment of the invention to provide an interface unit with epicardial lead protection from the environment while also allowing the user to easily connect the epicardial leads to the terminals of the unit by placing the terminals proximate to the insertion openings.

The shroud may be movable with respect to the housing along the insertion axis.

It is thus a feature of at least one embodiment of the invention to allow for insertion of the epicardial wires into the unit and moving of the protective shroud without disturbing the wires.

The housing may provide a front and rear opposed surface and wherein the apertures of the first and second terminals are on a front surface and the first electrical connector is on an opposed rear surface so that the first and second epicardial wires and the first connector from the pacemaker connector may extend parallel to a common axis.

It is thus a feature of at least one embodiment of the invention to provide a more intuitive connection of the leads/connectors to the interface unit with less bending of wires.

The housing may further provide opposed upper and lower surfaces wherein the second electrical connector is on the upper surface It is thus a feature of at least one embodiment of the invention to visually isolate each electrical connector on the unit and allow the ECG monitor connector to be accessible when the unit is resting on the patient's chest.

Buttons may be used to capture the first and second epicardial lead wires.

It is thus a feature of at least one embodiment of the invention to require zero insertion force for insertion of the wires because the connector holes are amply oversized, and the pinching force on the wires is applied by spring-loaded buttons. The connector holes also accommodate epicardial wires of varying sizes and diameters.

The buttons may be on left and right opposed surfaces of the housing.

It is thus a feature of at least one embodiment of the invention to allow the epicardial wires to be removed spatially from the other connectors and attachable without pressing downwards on the patient. Also, this feature allows for rapid release of epicardial wires by simultaneously grasping both buttons.

The buttons may be biased by a spring to capture the first and second epicardial lead wires. The buttons may be opposed first and second buttons biased away for each other by a shared spring.

It is thus a feature of at least one embodiment of the invention to allow for single-handed capture and release of the epicardial wires. Also, the spring force may allow the wires to be removed at a high force that is less than the force to remove the wires from the heart.

The actuation axis may be orthogonal to the insertion axis.

It is thus a feature of at least one embodiment of the invention to use a natural grip angle for actuation of the side buttons. Also, the feature allows for inadvertent movement of the housing caused by button presses to not dislodge the wires.

The buttons may provide a blocking arm extending into the housing and positioned between the first and second electrical terminal and the first and second aperture in a first position and provide a path between the first and second electrical terminal and the first and second aperture in a second position. The blocking arm may include a window that is aligned along the insertion axis when the button is in the second position It is thus a feature of at least one embodiment of the invention to block the terminals from environmental exposure when the wires are not attached.

The circuit may provide a resistance of at least 50 kilo-ohms.

It is thus a feature of at least one embodiment of the invention to allow the unit to work with a variety of telemetry monitors with different degrees of electrical protection (e.g., Type CF (cardiac flowing) classification).

A tethered cover may cover at least one of the first and second connector.

It is thus a feature of at least one embodiment of the invention to prevent accidental shorting when the pacemaker is not used.

Fiducial labels of plus and minus signs may be positioned proximate the first and second apertures respectively.

It is thus a feature of at least one embodiment of the invention to provide intuitive connection of positive and negative wires of the epicardial leads to prevent confusion.

A detent may be positioned between the housing and the shroud in at least one of the first and second positions.

It is thus a feature of at least one embodiment of the invention to maintain the shroud in the extended, protective position when the epicardial lead wires are attached to the unit.

The second electrical connector is a stud connector defined by a metallic boss extending outwardly from the housing and electrically coupled to the circuit assembly, wherein the stud connector is positioned on an exterior of the housing.

It is thus a feature of at least one embodiment of the invention to connect with a variety of standard ECG monitor connectors.

The present invention provides, in another aspect, a pace generator providing electrical impulses configured to provide electrical pacing to a heart of a patient through epicardial pacing leads connected to the heart; a telemetry monitor configured to receive electrical cardiac signals from the epicardial pacing leads to provide a display of the electrical cardiac signals; and an interface unit including: an electrically insulating housing; a first and second electrical terminal accessible through corresponding apertures in the housing and adapted to releasably receive a first and second epicardial lead wires to an interior of the housing parallel to an insertion axis; a first electrical connector attached to the insulating housing to releasably receive a pacemaker connector at third and fourth electrical terminals; a second electrical connector attached to the insulating housing to receive a telemetry monitor connection at a fifth terminal; a circuit positioned within the housing, the circuit providing electrical communication between the second and third electrical terminals and between the first, fourth terminal and the fifth terminal; and an electrically insulating shroud providing a first and second aperture for receiving the first and second epicardial wire therethrough before the first and second epicardial wire is received by the first and second electrical terminal and movably attached to the housing to move between a first position proximate to the first and second terminal and a second position removed from the first and second terminal providing an insulating cover over the first and second epicardial wire extending outward from the first and second terminals.

It is thus a feature of at least one embodiment of the invention to allow the pacemaker to be optionally connected to the interface unit during electrogram visualization.

The first aperture and first terminal may be aligned along a first insertion axis and the second aperture and second terminal may be aligned along a second insertion axis, and the first and second insertion axes may be spaced apart in parallel.

It is thus a feature of at least one embodiment of the invention to isolate each of the positive and negative aperture and terminal to prevent shorting and misconnection.

The present invention provides, in another aspect, a connector including a housing with an aperture, and a circuit assembly positioned within the housing. The circuit assembly includes a circuit board with a terminal. The connector further includes a shroud movable with respect to the housing between a first position and a second position. The housing is positioned at least partially within the shroud. The connector further includes a button including a blocking arm positioned between the terminal and the aperture. The button is movable along an actuation axis between a blocking position and a non-blocking position. The connector further includes a biasing member biasing the button toward the blocking position.

The present invention provides, in another aspect, a connector including a housing with a first aperture and a second aperture, and a circuit assembly positioned within the housing. The circuit assembly includes a circuit board with a first terminal and a second terminal. The connector further includes a shroud at least partially enclosing the housing, the shroud including a first exterior aperture and a second exterior aperture. The first aperture, the first terminal, and the first exterior aperture are aligned along a first insertion axis and the second aperture, the second terminal, and the second exterior aperture are aligned along a second insertion axis. The housing is positioned at least partially within the shroud.

The present invention provides, in another aspect, a connector including a housing with an aperture, and a circuit assembly positioned within the housing. The circuit assembly includes a circuit board with a terminal defining an insertion axis. The connector further includes a button coupled to the housing. The button defines a blocking portion and a window, wherein the button is movable along an actuation axis between a blocking position and a non-blocking position. The actuation axis is orthogonal to the insertion axis. The connector further includes a biasing member biasing the button toward the blocking position. The blocking portion of the button is positioned between the aperture and the terminal when the button is in the blocking position, and wherein the window of the button is positioned between the aperture and the terminal when the button is in the non-blocking position.

These particular objects and advantages may apply to only some embodiments falling within the claims and thus do not define the scope of the invention.

Other features and aspects of the invention will become apparent by consideration of the following detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

DETAILED DESCRIPTION OF THE PREFERRED EMBODIMENT

Figure 1:
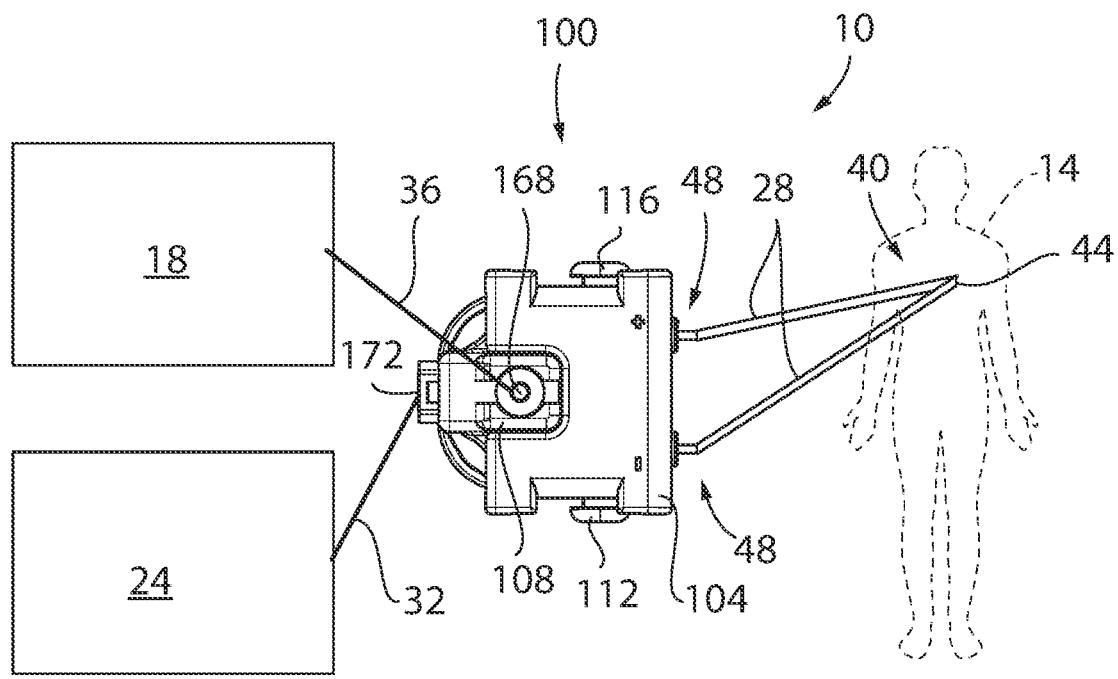
FIG. 1 is a schematic view of a medical system with a connector in accordance with one embodiment of the invention showing connection of the connector to an ECG monitor, pacemaker, and patient.

With reference to FIG. 1, a medical system 10 for the care of a patient 14 includes an electrocardiographic (ECG) monitor 18, a pacemaker 24, a plurality of pacing wires 28, and a connector 100. The connector 100 (i.e., adaptor, coupling, etc.) is configured to interface with the multiple medical devices of the medical system 10. For example, the connector 100 may be configured to interface with (i.e., provides connections for, interconnects, etc.) the plurality of pacing wires 28, the pacemaker 24, and the ECG monitor 18. More specifically, the pacemaker 24 is electrically coupled to the connector 100 by a pacemaker cord 32 (shown in FIG. 9), the ECG monitor 18 is electrically coupled to the connector 100 by an ECG leadwire 36, and the patient 14 is electrically coupled to the connector 100 by the plurality of pacing wires 28 as described in further detail below. Aspects of such an integrated medical system are disclosed in U.S. patent application Ser. No. 15/229,371, the contents of which are incorporated herein in their entirety.

Figure 2:
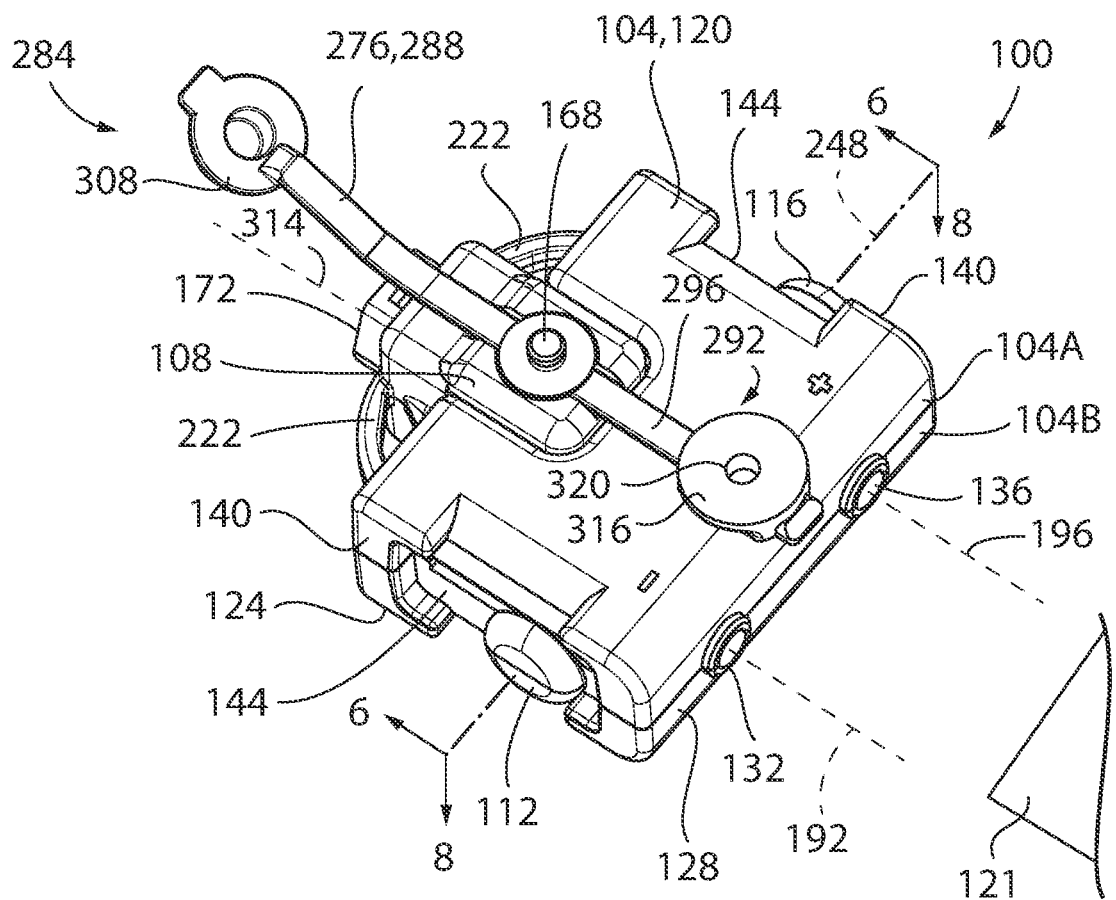
FIG. 2 is a top perspective view of the connector of FIG. 1.
Figure 3:
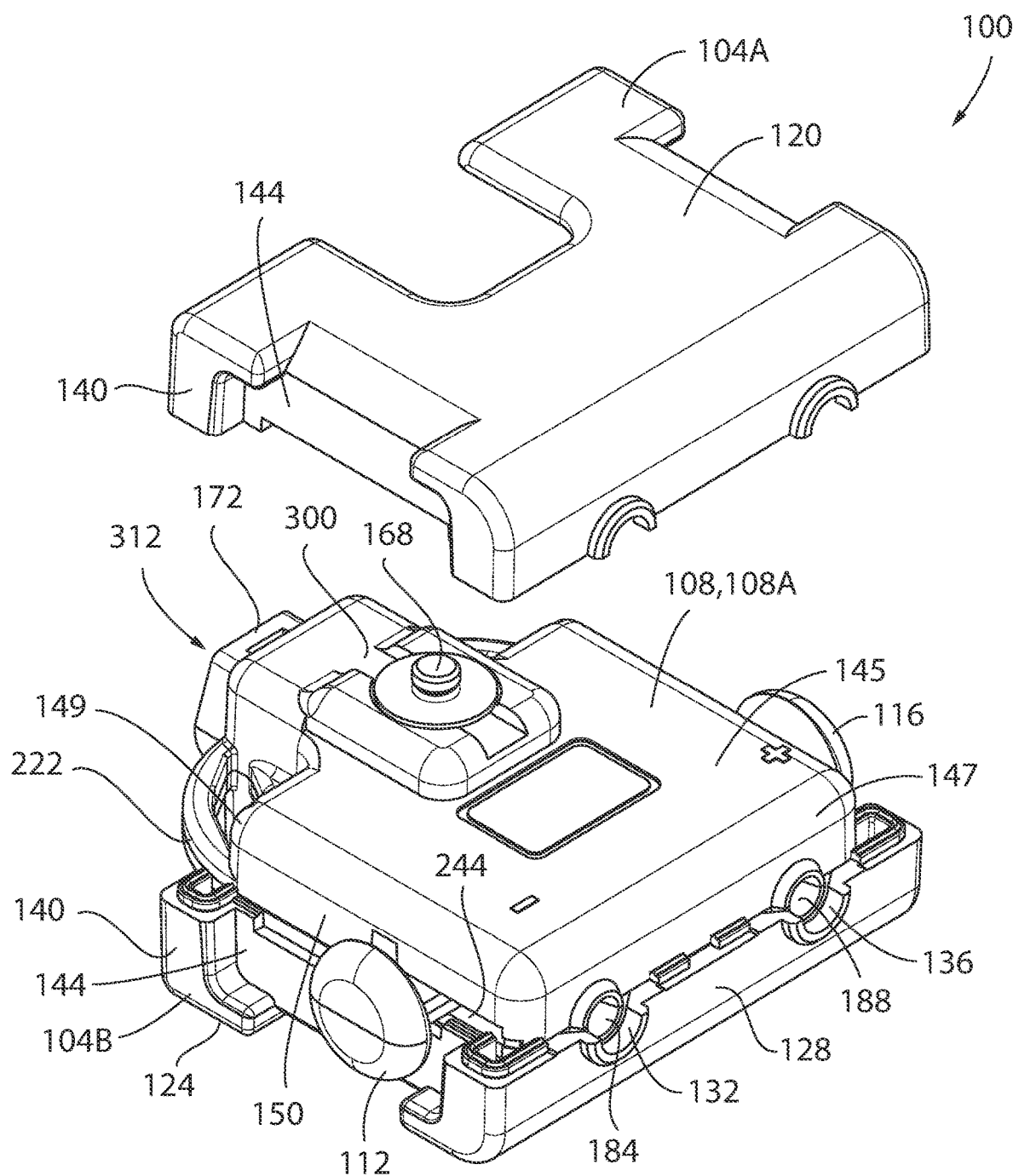
FIG. 3 is a top perspective view of the connector of FIG. 1 with a portion of a shroud of the connector removed from the connector inner housing.
Figure 4:
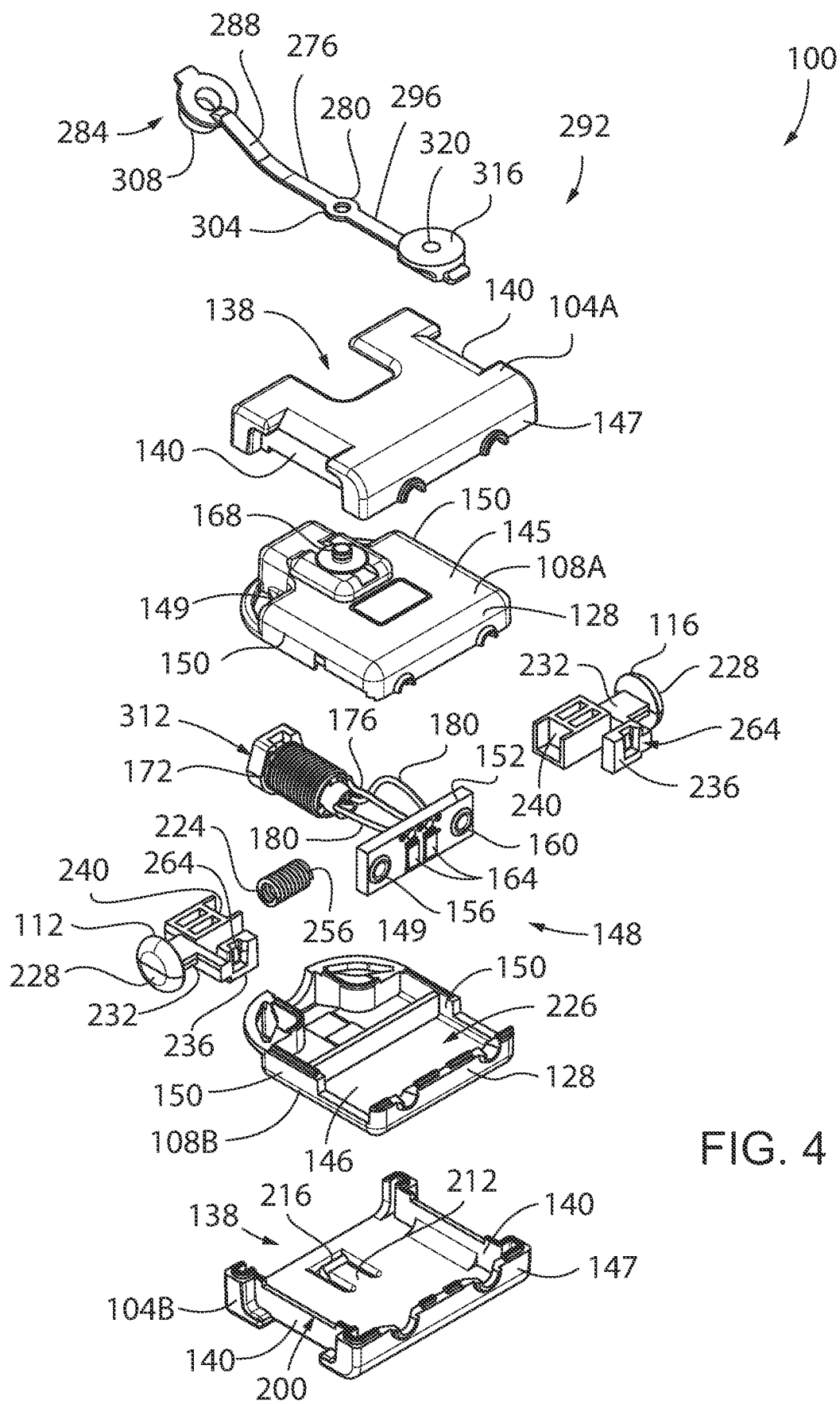
FIG. 4 is an exploded view of the connector of FIG. 1.

With reference to FIGS. 2 to 4, the connector 100 includes an outer shroud 104, an inner housing 108 slidably positioned at least partially within the shroud 104, and a first button 112 and a second button 116 extending outwardly from the outer shroud 104 and inner housing 108. In the illustrated embodiment, the shroud 104 is a generally rectangular casing formed by joining, for example, by bonding or welding, top and bottom members 104A, 104B and the inner housing 108 is a generally rectangular box likewise formed by joining, for example, by bonding or welding, top and bottom members 108A, 108B (FIG. 3). The outer shroud 104 and inner housing 108 may be made from biocompatible and gamma compatible materials. In one embodiment, the outer shroud 104 may be an electrically insulating plastic such as polycarbonate-ABS (PC-ABS) and the inner housing may be an electrically insulating plastic such as polybutylene terephthalate (PBT). The outer shroud 104 and inner housing 108 may be colored in a non-white color to designate the connector for atrial pacing and not ventricular pacing (designated white), for example, the outer shroud 104 may be blue and the inner housing 108 may be grey. It is understood that other compatible materials and colors may be used.

With specific reference to FIGS. 3 and 4, the shroud 104 includes a top wall 120 extending along a plane parallel to a plane 121 of a chest of the patient 14 and generally spaced away from the chest of the patient 14, a bottom wall 124 extending along a plane parallel to the plane 121 of the chest of the patient 14 and generally abutting the chest of the patient 14, and a front wall 128 extending perpendicular to the plane 121 of the chest of the patient 14 and generally positioned inferiorly on the patient 14. In addition, the shroud 104 includes sidewalls 140 joining the top wall 122 and the bottom wall 124 at left and right edges, respectively, the sidewalls 140 carrying a rectangular opening defining a track 144 receiving the corresponding buttons 112, 116 discussed in further detail below.

The front wall 128 provides a first exterior aperture 132 and a second exterior aperture 136 where the first exterior aperture 132 and second exterior aperture 136 are round holes spaced apart and receiving the proximate ends 48 of the pacing wires 28. The holes may have a diameter of at least 0.9 mm and at least 1 mm and may be approximately 1.5 mm. The holes may have a diameter that is generally greater than a largest diameter of the end rods 52 of the pacing wires 28 to accommodate insertion of different wire sizes.

In the illustrated embodiment, a rear end 138 of the shroud 104 is generally open (i.e., not enclosed) to allow the housing 108 to be slidably received within the rear end 138 of the shroud 104. In alternative embodiments, however, the inner housing 108 may be completely enclosed by the shroud 104. As explained in greater detail below, the shroud 104 is moveable with respect to the housing 108 between a first, retracted position (FIG. 8A) and a second, extended position (FIG. 8D) in order to block the proximate ends 48 of the pacing wires 28.

The housing 108 includes a top wall 145 extending parallel to the plane 121 of a chest of the patient 14 and generally spaced away from the chest of the patient 14, a bottom wall 146 extending parallel to the plane 121 of the chest of the patient 14 and generally abutting the chest of the patient 14, a front wall 147 extending perpendicular to the plane 121 of the chest of the patient 14 and generally positioned inferiorly on the patient 14, and a rear wall 149 extending perpendicular to the plane 121 of the chest of the patient and generally positioned superiorly on the patient 14. In addition, the housing 108 includes sidewalls 150 joining the top wall 145 and the bottom wall 146 at left and right edges, respectively.

The front wall 147 includes a first aperture 184 and a second aperture 188 where the first aperture 184 and the second aperture 188 are round holes spaced apart and receiving the proximate ends 48 of the pacing wires 28. The holes may have a diameter of at least 0.9 mm and at least 1 mm and may be approximately 1.5 mm. The holes may have a diameter that is generally greater than a largest diameter of the end rods 52 of the pacing wires 28 to accommodate insertion of different wire sizes. The first aperture 184 and second aperture 188 may have a greater diameter than the first exterior aperture 132 and a second exterior aperture 136.

The first aperture 184 and the second aperture 188 may correspond with the positioning of the first exterior aperture 132 and the second exterior aperture 136 of the shroud 104 and are configured to receive the proximate ends 48 of the pacing wires 28. The first aperture 184, and the first exterior aperture 132 are aligned along a first insertion axis 192. Likewise, the second aperture 188, and the second exterior aperture 136 are aligned along a second insertion axis 196. In other words, the first aperture 184 is coaxially aligned with the first terminal 156, and the first exterior aperture 132 is coaxially aligned with the first aperture 184. Likewise, the second aperture 188 is coaxially aligned with the second terminal 160, and the second exterior aperture 136 is coaxially aligned with the second aperture 188. As such, the first insertion axis 192 is defined by each of the first terminal 156, the first aperture 184, and the first exterior aperture 132 independently and collectively. Likewise, the second insertion axis 196 is defined by each of the second terminal 160, the second aperture 188, and the second exterior aperture 136 independently and collectively. The first and second insertion axis 192, 196 extend substantially parallel to the plane 121 of the patient's chest.

In the illustrated embodiment, the first insertion axis 192 is desirably spaced apart from and parallel to the second insertion axis 196. In one embodiment, the first insertion axis 192 is spaced apart from the second insertion axis 196 by at least 20 mm or at least 25 mm or at least 30 mm. In one embodiment, the first insertion axis 192 is spaced apart from the second insertion axis 196 by a distance at least three to six times the distance between the front wall 128 of the shroud 104 and the terminals 156, 160 when the shroud 104 is in the second position (FIG. 8D). In alternative embodiments, the first insertion axis 192 and the second insertion axis 196 intersect but do not allow the pacing wires 28 to touch.

Figure 8A:
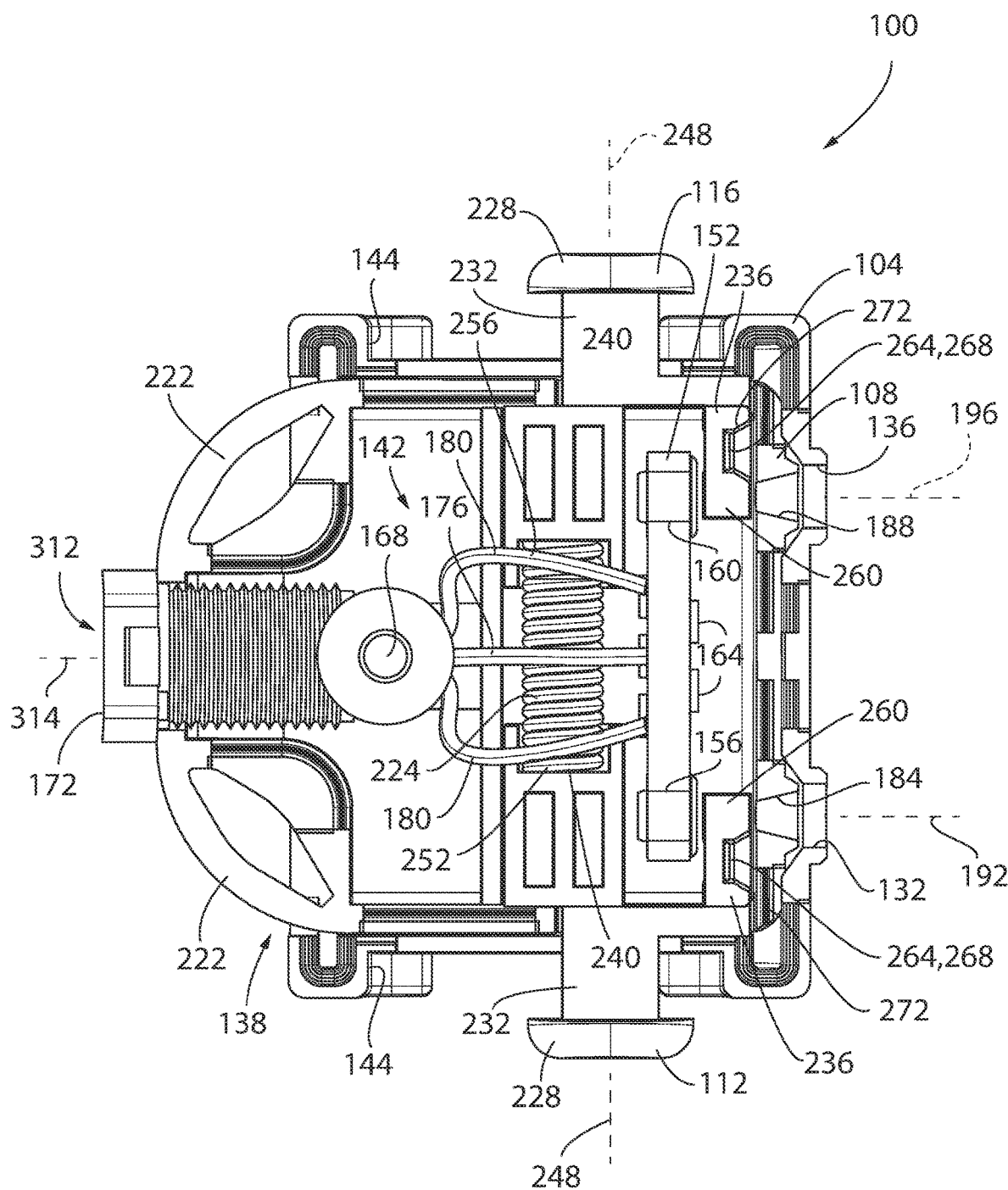
FIG. 8A is a cross-sectional view of the connector of FIG. 1 taken along line 8-8 of FIG. 2, with buttons released in a hole blocking position and a shroud in a first, retracted position.
Figure 8B:
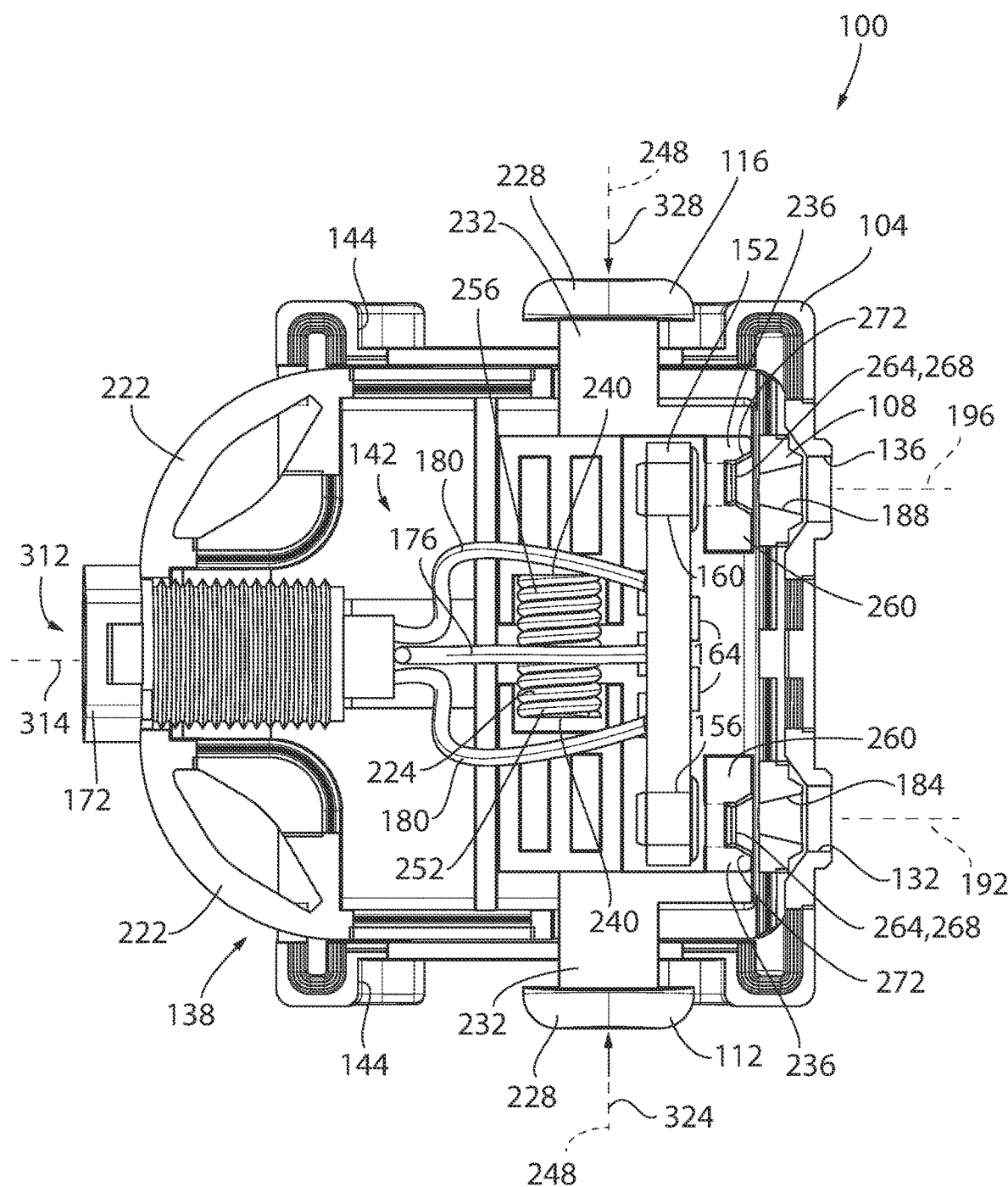
FIG. 8B is a cross-sectional view of the connector of FIG. 1 taken along line 8-8 of FIG. 2, with the buttons depressed in a non-hole blocking position and the shroud in the first, retracted position.
Figure 8C:
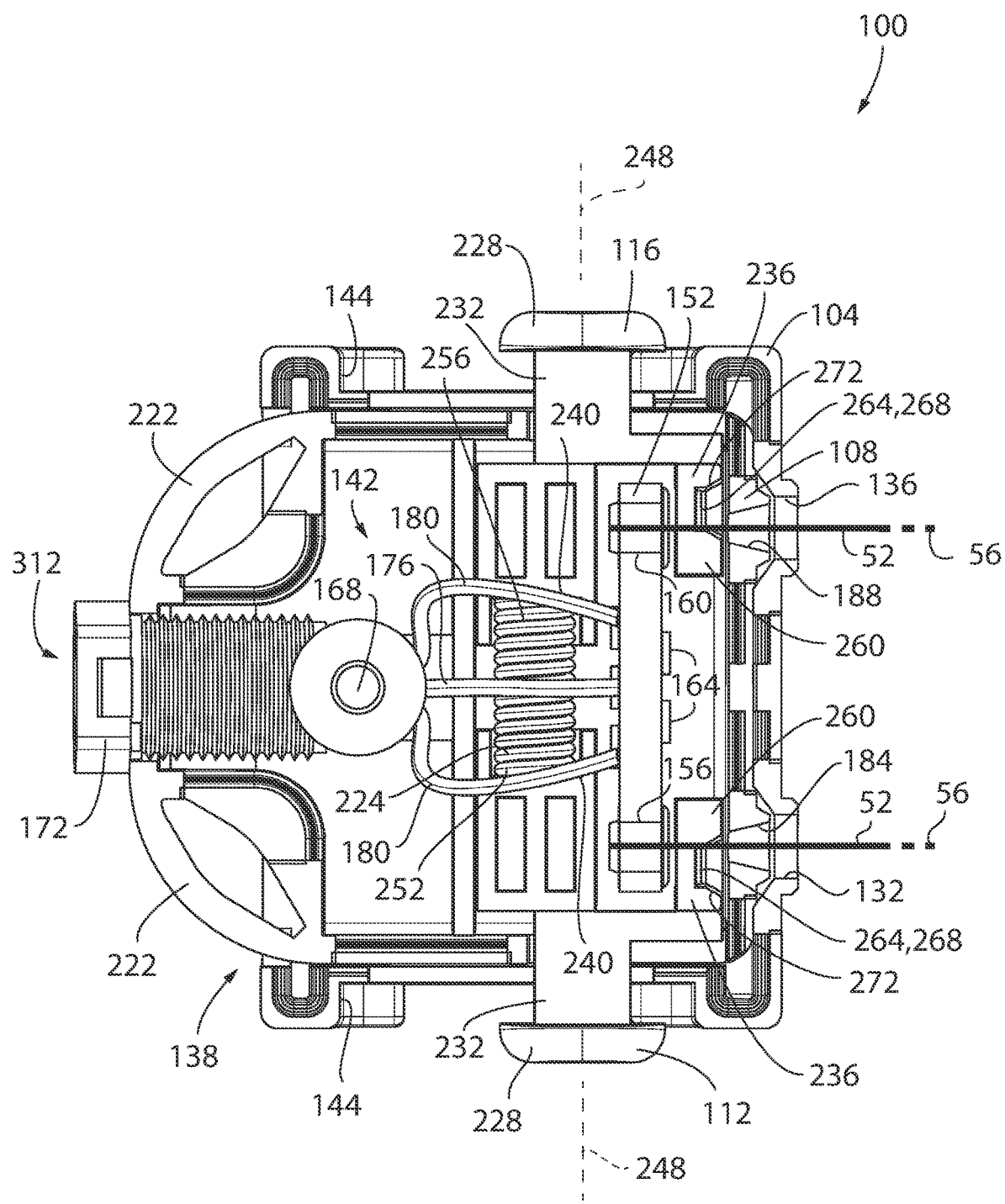
FIG. 8C is a cross-sectional view of the connector of FIG. 1 taken along line 8-8 of FIG. 2, with the buttons released with wires in the holes and the shroud in the first, retracted position.
Figure 8D:
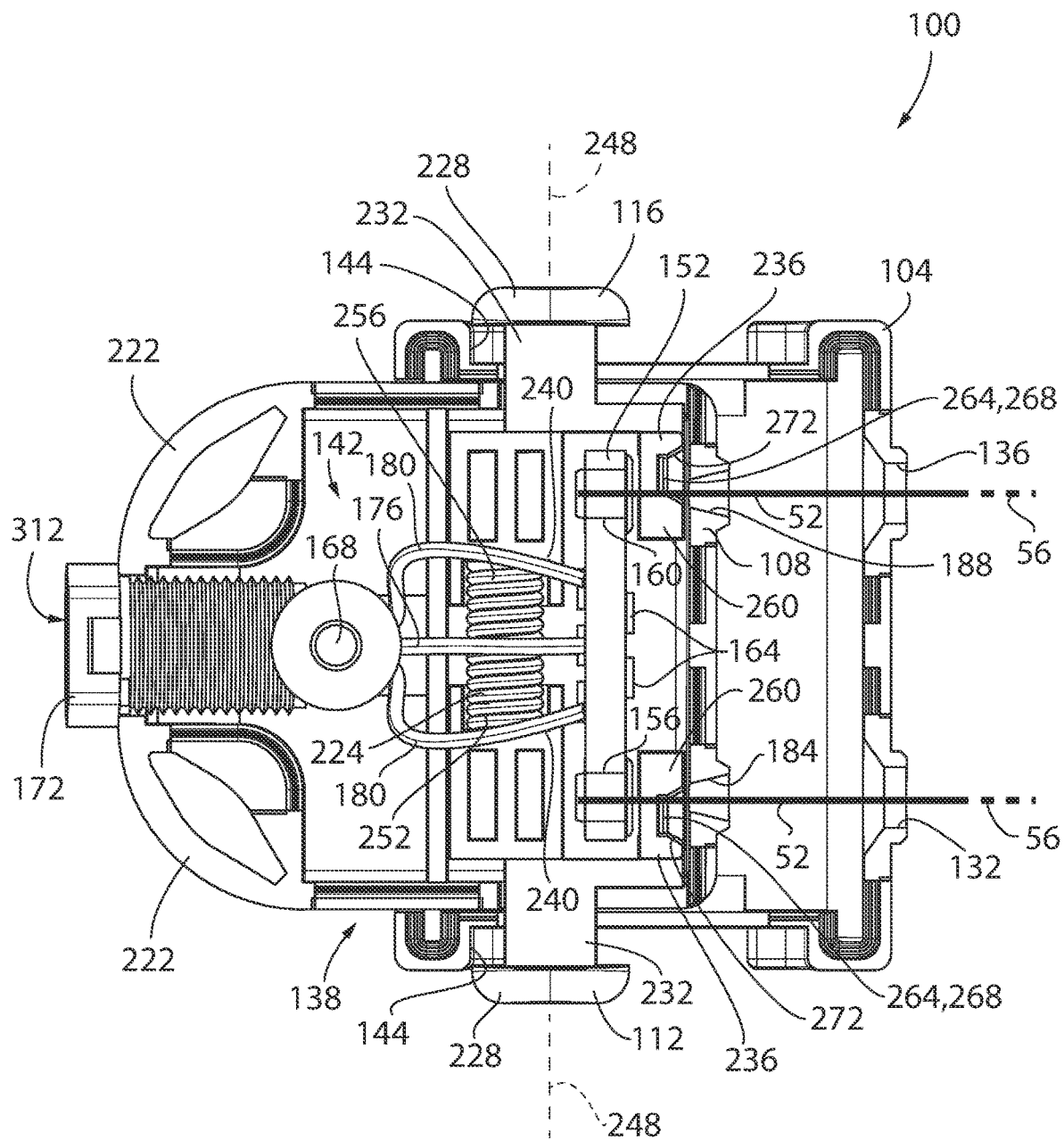
FIG. 8D is a cross-sectional view of the connector of FIG. 1 taken along line 8-8 shown in FIG. 2, with the buttons released with wires in the holes and the shroud in a second, extended position.

Referring to FIGS. 8A to 8D, and as explained in greater detail below, a user is able to move and selectively position the shroud 104 in the first, retracted position (FIG. 8A), in the second, extended position (FIG. 8D), or in any intermediate position there between. In other words, the shroud 104 is movable (e.g., slidable) with respect to the housing 108 along the first insertion axis 192 and the second insertion axis 196. When the shroud 104 is in the second position (FIG. 8D), the front wall 128, and the first and second exterior aperture 132, 136 held by the front wall 128, positioned further away from the terminals 156, 160 than when the shroud 104 is in the first position (FIG. 8A). In one embodiment, when the shroud 104 is in the second position (FIG. 8D), the front wall 128 is positioned at least 4 mm away or at least 5 mm away or at least 6 mm away from the terminals 156, 160.

Figure 7:
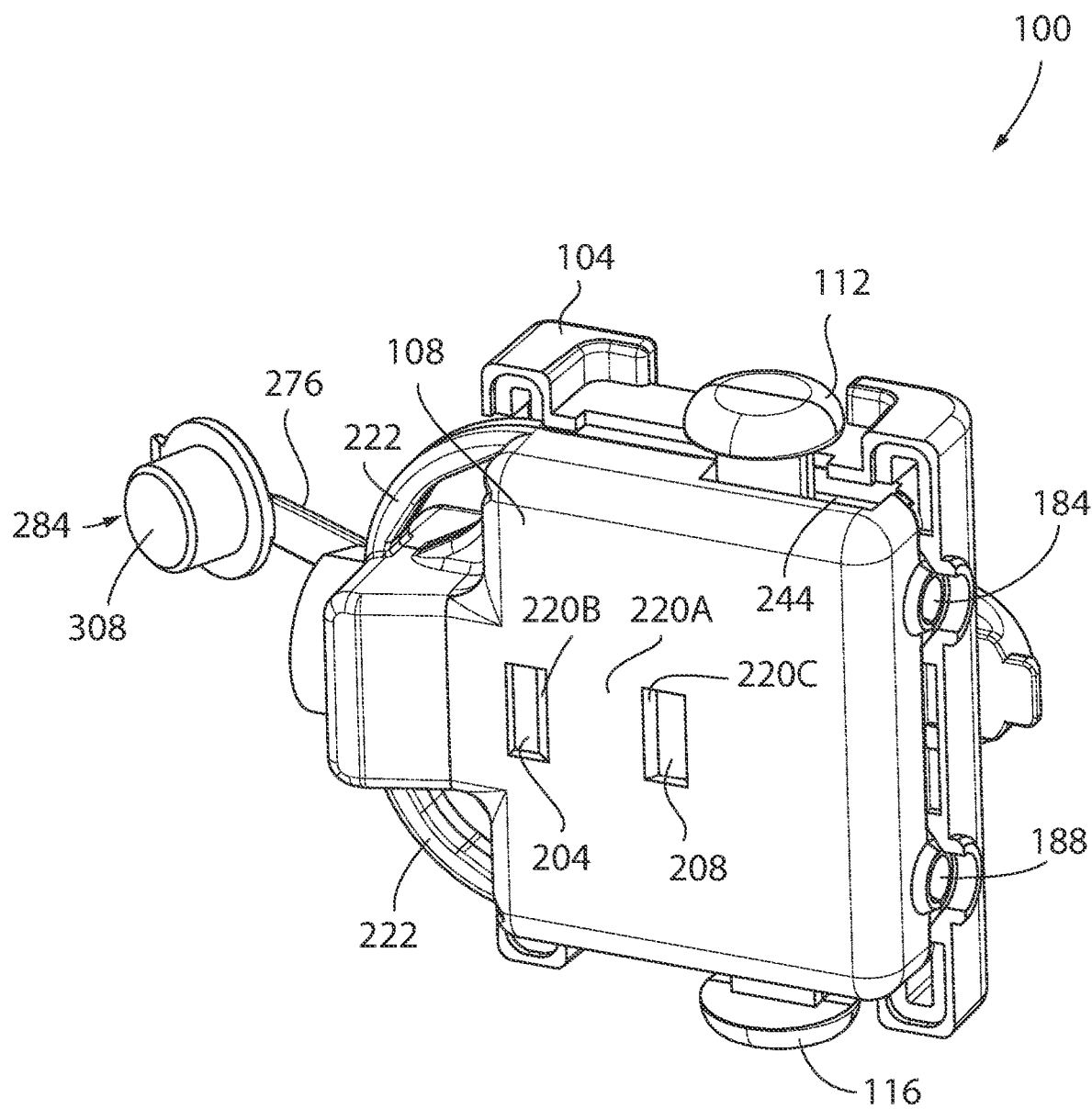
FIG. 7 is a bottom perspective view of the connector of FIG. 1 with portions removed for clarity.

With reference also to FIGS. 4 and 7, an inner surface of the bottom wall 124 of the shroud 104 includes a detent 200 that is received within a first recess 204 (i.e., a first track) formed on an outer surface of the bottom wall 146 of the housing 108 when the shroud 104 is in the first, retracted position (FIG. 8A) and is received within a second recess 208 (i.e., a second track) formed on the housing 108 when the shroud 104 is in the second, extended position (FIG. 8D). In alternative embodiments, the detent 200 is formed on the housing 108 and the corresponding recesses 204, 208 are formed on the shroud 104.

In the illustrated embodiment, the detent 200 is a cantilevered spring arm 212 formed on the shroud 104 and having an inwardly biased protrusion 216 formed thereon at a tip of the cantilevered spring arm 212 (FIG. 4). The first recess 204 is positioned adjacent to the second recess 208 on the outer surface of the bottom wall 146 of the housing 108, with the second recess 208 positioned closer to the apertures 184, 188 than the first recess 204. A plurality of cam surfaces 220 are formed on the housing 108 and are positioned between the first recess 204 and the second recess 208. In the illustrated embodiment, three cam surfaces 220 are positioned between the first recess 204 and the second recess 208, the first cam surface 220a extending between the first recess 204 and the second recess 208, the second cam surface 220b extending upwards from the first recess 204 to the first cam surface 220a, and the third cam surface 220c extending downwards from the first cam surface 220a to the second recess 208.

When the shroud 104 is in the retracted position (FIG. 8A), the protrusion 216 of the detent 200 is received within the first recess 204 formed on the housing 108. A predetermined amount of force is applied to the shroud 104 along the insertion axes 192, 196 to move the protrusion 216 upward along cam 220b and out of the first recess 204. The momentum of the force causes the protrusion to move to the extended position (FIG. 8D). The shroud 104 remains in the retracted position (FIG. 8A) during insertion of the end rods 52 of the pacing wires 28 into the shroud 104 until the predetermined amount of force of applied, preventing inadvertent movement of the shroud 104 during installation.

As the shroud 104 moves to the extended position (FIG. 8D) along the insertion axes 192, 196, the shroud 104 is moved away from the housing 108, and the spring arm 212 deflects away from the housing 108 as the protrusion 216 cams along the ramped cam surfaces 220b, 220a, 220c, respectively, and is eventually received from cam surface 220a along downwardly extending cam surface 220c into the second recess 208. The second recess 208 is sized to tightly receive the inwardly biased protrusion 216. A wall of the second recess 208 opposite the cam surface 220c is substantially perpendicular to the bottom surface of the second recess 208 to restrict further movement of the protrusion 216 along the insertion axes 192, 196. As such, the protrusion 216 is selectively fixed within the second recess 208, thereby holding the shroud 104 in the extended position (FIG. 8D).

The shroud 104 is held in the extended position (FIG. 8D) until a user applies a threshold level of force to the shroud 104. In particular, the user applies a threshold level of force along the insertion axes 192, 196, forcing the housing 108 and shroud 104 toward each other, to move the shroud 104 back towards the retracted position (FIG. 8A). More specifically, a threshold level of force is applied to the shroud 104 to cause the spring arm 212 to deflect and the protrusion 216 to slidably cam back across the cam surface 220 back into the first recess 204.

In one embodiment, the threshold level of force needed to cause the spring arm to want to deflect and the protrusion 216 slidably cam back across the cam surface 220 back into the first recess 204 is greater than the threshold level of force needed to deflect the spring arm 212 away from the housing 108 as the protrusion 216 cams along the cam surfaces 220 to be received within the second recess 208. In other words, the level of force needed to move the shroud 104 to the extended position (FIG. 8D) is less than the level of force needed to move the shroud 104 back to the retracted position (FIG. 8A)

With reference to FIGS. 3 and 4, the connector 100 further includes a biasing member 224 (e.g., a coil spring) that is positioned within the housing 108 and is positioned between opposed first button 112 and second button 116. The first button 112 and the second button 116 are partially received within the housing 108 and are held within a rectangular cavity 226 within the housing 108. The first button 112 and the second button 116 extend out of the housing 108 and are positioned within the track 144 of the shroud 104 to slide therealong when the shroud 104 is moved between the extended position (FIG. 8D) and the retracted position (FIG. 8A). In the illustrated embodiment, the first button 112 is functionally identical to the second button 116 but is a mirrored reflection of the first button 112, and therefore, any description of the first button 112 is likewise applicable to the second button 116 except for having a mirrored geometry. However, in alternative embodiments, variations between the first button 112 and the second button 116 may exist.

Figure 5:
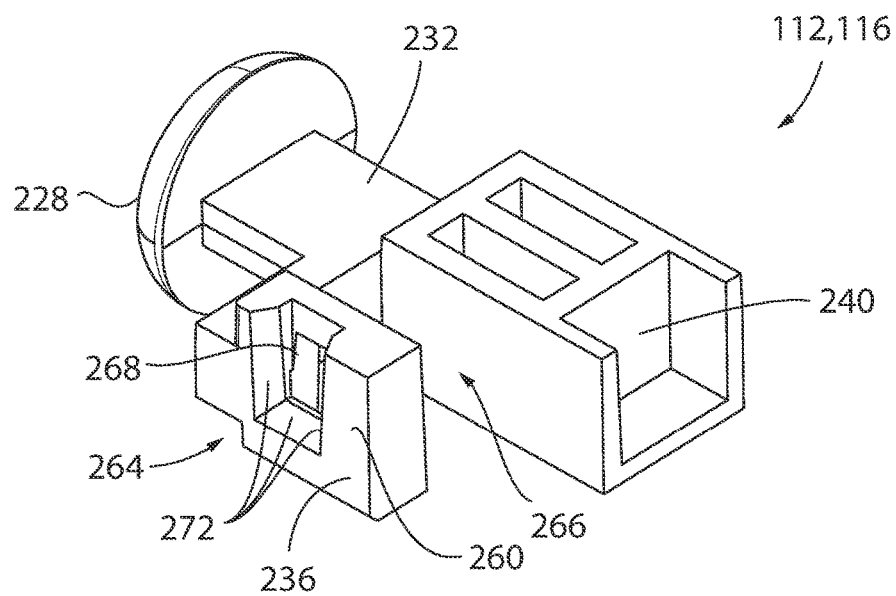
FIG. 5 is a perspective view of one of the opposed buttons of the connector of FIG. 1.
Figure 6:
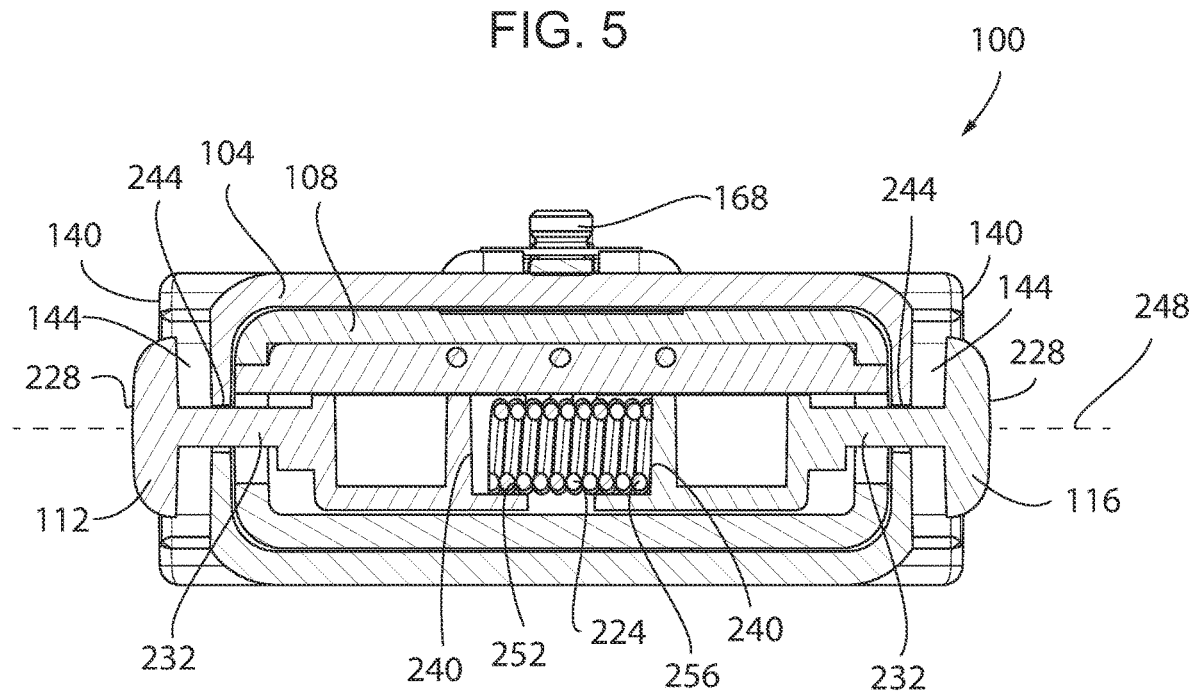
FIG. 6 is a cross-sectional view of the connector of FIG. 1 taken along the line 6-6 of FIG. 2 exposing the opposed buttons biased outward by a spring.

With reference to FIG. 5, the first button 112 is shown in isolation for clarity. The button 112 includes a user-actuated portion 228, a stem 232, a blocking arm 236, and a seat 240 (i.e., a spring seat). With reference to FIG. 3, the blocking arm 236 and the seat 240 are coupled to and positioned within the housing 108, the stem 232 extends out of the housing 108, and the user-actuated portion 228 is positioned outside the housing 108 and outside of the shroud 104. In particular, the stem 232 extends through a slot 244 formed in the housing 108, and the user-actuated portion 228 is received within the track 144 formed in the shroud 104. In the illustrated embodiment, the user-actuated portion 228 is rounded and configured to be actuated along an actuation axis 248 by a user (i.e., by depressing the user-actuated portion 228). The stem 232 connects the user-actuated portion 228 to the seat 240 and the blocking arm 236. The seat 240 is configured to receive or otherwise support the biasing member 224. In the illustrated embodiment, the seat 240 is formed as a recess. In alternative embodiments, the seat 240 may be, for example, a post around which the biasing member 224 is seated.

As explained in greater detail below, in response to actuation of the user-actuated portion 228, the button 112 moves along the actuation axis 248 between a blocking position (FIG. 8A) and a non-blocking position (FIG. 8B). In other words, in response to user actuation, i.e., pressing, of the button 112, the button 112 moves further within the housing 108 along the actuation axis 248. The biasing member 224 biases the button 112 toward the blocking position (FIG. 8A), such that the button 112 automatically moves back towards the blocking position (FIG. 8A) once a user releases the user-actuated portion 228. In the illustrated embodiment, the actuation axis 248 is orthogonal to the first insertion axis 192 and the second insertion axis 196. In alternative embodiments, the actuation axis 248 is non-orthogonal to either the first insertion axis 192 and/or the second insertion axis 196.

With reference to FIGS. 6 and 8A to 8C, the biasing member 224 (e.g., a coil spring) is positioned between the first button 112 and the second button 116, biasing both the first button 112 and the second button 116 toward the blocking position (FIG. 8A). In particular, a first end 252 of the biasing member 224 is received within the seat 240 of the first button 112, and a second, opposite end 256 of the biasing member 224 is received within the seat 240 on the second button 116. The coil spring may have ground ends to stabilize the biasing member 224 between the opposed seats 240 of the first button 112 and second button 116 and to prevent rotation of the coil spring.

Like the first button 112, the second button 116 is movable along the actuation axis 248 between a blocking position (FIG. 8A) and a non-blocking position (FIG. 8B). In the illustrated embodiment, the first button 112 is movable with respect to the housing 108 independent of the second button 116. In other words, the first button 112 may move along the actuation axis 248 without necessarily moving the second button 116, and vice versa. As explained in greater detail below, the buttons 112, 116 are also movable to any intermediate position between the blocking position (FIG. 8A) and the non-blocking position (FIG. 8B). As an example of an intermediate position, the buttons 112, 116 are movable to a capturing position (FIG. 8C). As explained in greater detail below, the buttons 112, 116 secure end rods 52 of the pacing wires 26 within the connector 100 when the buttons 112, 116 are in the capturing position (FIG. 8C).

With continued reference to FIG. 5, a blocking arm 236 of the button 112 is spaced away from the seat 240 of the button 112 and extends along the front wall 147 of the housing 108 and includes a blocking portion 260 and a window 264. The window 264 includes an opening 268 formed through the blocking arm 236 and a plurality of beveled surfaces 272 adjacent to the opening 268. A space 266 formed between the seat 240 and the blocking arm 236 of the button 112 supports the circuit assembly 148 as further described below.

With reference to FIG. 8A, the circuit assembly 148 is positioned between the blocking arm 236 and the housing 108. More specifically, the blocking arm 236 of the first button 112 is positioned between the first terminal 156 and the first aperture 184. Likewise, the blocking arm 236 of the second button 116 is positioned between the second terminal 160 and the second aperture 188. When the button 112 is in the blocking position (FIG. 8A), the blocking portion 260 of the blocking arm 236 is positioned between and aligned with the first aperture 184 and the first terminal 156. Likewise, when the button 112 is in the non-blocking position (FIG.

8B), the window 265 of the blocking arm 236 is positioned between and aligned with the first aperture 184 and the first terminal 156.

The circuit assembly 148 is positioned within the housing 108 and is held within the space 266 of the first button 112 and second button 116. The circuit assembly 148 includes a rectangular circuit board 152 extending parallel to the front wall 128 and holding a first terminal 156 and a second terminal 160. A substrate of the rectangular circuit board 152 may be approximately 3 mm to 4 mm in thickness, which is about double the average thickness of a typical circuit board, thus providing additional strength and insertion contact depth. The substrate of the rectangular circuit board 152 may be a glass fiber reinforced epoxy resin with a copper foil bond on one or both sides. The substrate of the rectangular circuit board 152 may also include more than one layer, for example, as much as thirty layers of glass fiber reinforced epoxy resin with a copper foil bond on one or both sides bonded by prepregs (bonding sheets).

Figure 10:
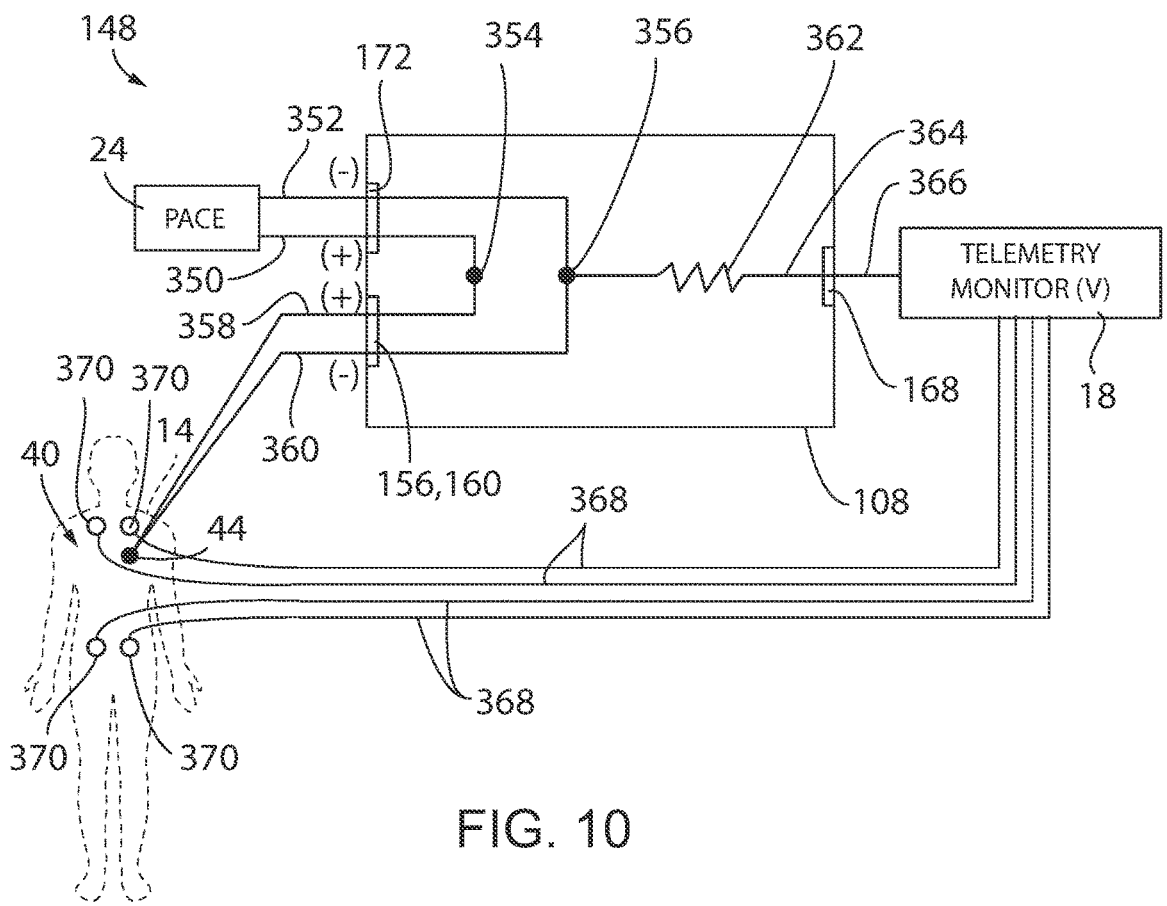
FIG. 10 is a schematic of the circuit assembly of the connector used to condition the electrical signals.

Referring to FIGS. 4 and 10, the circuit assembly 148 may include a protective signal conditioning circuit. In the illustrated embodiment, the circuit assembly 148 includes resistors 164 to passively condition electrical signals passing through the circuit assembly 148. In other words, the resistors 164 prevent large, undesired current from flowing through the connector 100. More specifically, the resistors 164 prevent large current flowing through the connector 100 to the ECG monitor 18. In the illustrated embodiment, the circuit assembly 148 does not include any software or active decision circuitry, which simplifies the overall design and reduces overall costs. The printed circuits may be copper which is either plated or etched away on the surface of the substrate. The copper circuits may be coated with a layer of tin lead to prevent oxidation. Contact fingers may be plated with tin lead, nickel, and gold for conductivity.

Referring specifically to FIG. 10, the positive 350 and negative 352 wires of the pacemaker cord 32 connecting the pacemaker 24 may be received at pace generator connector 172 having female style receptacles 313 exposed through housing 108 and connecting respectively to junction points 354, 356 on the circuit assembly 148 held within the housing 108. The same junction points 354, 356 may also connect to the epicardial terminals 156, 160 exposed through the housing 108 and communicating with the positive 358 and negative 360 wires of the epicardial pacing wires 28. The junction points 354, 356 may connect to resistor 362 sized, for example, to be between 1 kilo-ohm and 50 kilo-ohms or 50 kilo-ohms or larger to prevent undue loading on the pacer signals by the circuit assembly 148. The resistor 362 may be a potentiometer with an adjustable voltage divider to vary the resistance. Following the resistor 362 the signal output 364 provides lead 366 accessible through a stud connector 168 to the ECG monitor 18. Specifically, the lead 366 is connected to the (V) terminal of the ECG monitor 18. A set of ECG connectors 368, for example four cables, may be attached to corresponding surface electrodes 370 placed on the chest of the patient 14 and further electrically coupled at an opposite end to the ECG monitor 18. The output signals of the set of ECG connectors 368 may combined (e.g., averaged) to synthesize a reference point (virtual ground) for the signal output 364 of lead 366.

Referring to FIG. 4, the first terminal 156 and the second terminal 160 are conductive, through-hole electrical connections formed in the circuit board 152, the holes extending parallel to the first exterior aperture 132 and the second exterior aperture 136 and perpendicular to the circuit board 152. The through-hole electrical connectors may be eyelets having a sharp inner edge allowing the first terminal 156 and the second terminal 162 to cut into the end rods 52 for better electrical contact with the pacing wires 28. In one embodiment, the eyelets may be brass eyelets which are tin plated to prevent oxidation or corrosion.

In some embodiments, the circuit assembly 148 may be held in place by a low-pressure overmold (not shown) potted within the housing 108 and around the circuit assembly 148. The overmold provides, among other things, electrical insulation, dirt and debris ingress protection, and additional structural support.

During surgery a distal end 40 of the pacing wires 28 are positioned on an outer layer of a patient's heart 44 (i.e., the epicardium), while a proximate end 48 of the pacing wires 28 remains accessible outside of the patient 14. The exposed, proximate ends 48 of the pacing wires 28 provide both a way to detect and monitor the cardiac rhythm (i.e., via the ECG monitor 18) and a way to send electrical signals to pace the heart (i.e., with the external pacemaker 24).

Referring to FIG. 8C, more specifically, the proximate end 48 of the pacing wires 28 include an exposed stiff end rod 52, and the end rod 52 is electrically coupled to the distal end 40 of the pacing wires 28 by an insulated wire portion 56 extending therebetween. It is understood that the end rod 52 may have varying diameters and lengths. For example, a diameter of the end rod 52 may vary between 0.8 mm to 2.2 mm, while a length of the end rod 52 may vary between 15 mm to 25 mm and may be approximately 23 mm.

As explained in greater detail below, the first terminal 156 and the second terminal 160 are configured to receive the exposed, proximate ends 48 of pacing wires 28. More specifically, the terminals 156, 160 are configured to receive and electrically connect to the end rods 52 of the pacing wires 28.

With continued reference to FIG. 4, the connector 100 further includes a stud connector 168 and a pace generator connector 172 positioned on an exterior of the housing 108. The stud connector 168 is electrically coupled to the circuit assembly 148 by at least one wire 176, and the pace generator connector 172 is electrically coupled to the circuit assembly 148 by wires 180.

More specifically, the top wall 145 of the housing 108 may support the stud connector 168 which is a metallic boss extending outwardly from the housing 108 and configured to connect to the ECG leadwire 36, which may utilize either a "snap" style or a "clip" style connection. The ECG leadwire 36 is electrically coupled to the stud connector 168 in order to monitor and display the cardiac rhythm detected by the epicardial pacing wires 28. The ECG monitor 18 is electrically coupled to the connector 100 by the ECG leadwire 36 which provides an electrical connection between the stud connector 168 and the circuit assembly 148.

The rear wall 149 of the housing 108 may support the pace generator connector 172 which may be, for example, a Hypertronic series connector (D Series) from Smiths Interconnect that may be compatible with the pacemaker cord 32 associated with, for example, a Medtronic Pacemaker. In other words, the pace generator connector 172 interfaces the epicardial pacing wires 28 with the external pacemaker 24.

The pace generator connector 172 may include a D-shaped receptacle with an interior cavity 312 receiving a connector of the pacemaker cord 32 therein along a third insertion axis 314 extending generally parallel to the plane 121 of the patient's chest and generally parallel to the first insertion axis 192 and second insertion axis 196 of the first aperture 184 and second aperture 188 respectively. The interior cavity 312 may include two female-style terminals 313 arranged in a lateral side-by-side configuration and configured to receive male-style contacts 315 of the pacemaker cord 32. The third insertion axis 314 may be found generally along the same plane as the first and second axes 192, 196.

In some embodiments, the pace generator connector 172 may be held in place by a low-pressure overmold (not shown) potted within the housing 108. The overmold provides, among other things, electrical insulation, dirt and debris ingress protection, and additional structural support.

Figure 9:
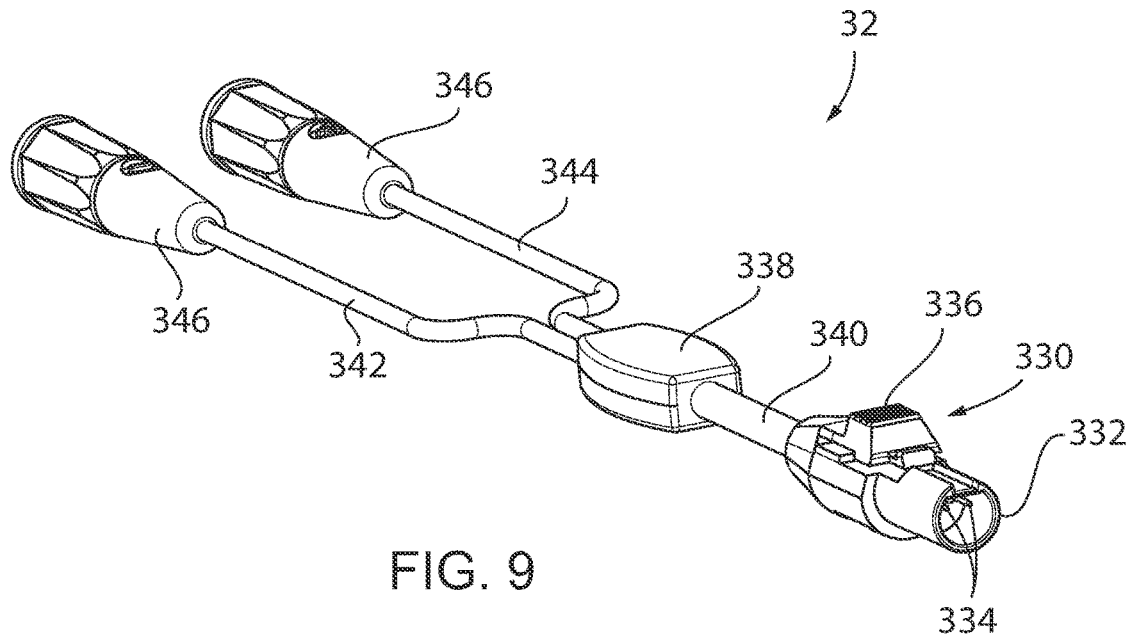
FIG. 9 is a perspective view of a pacemaker cord used to connect a pacemaker to the connector.

Referring to FIG. 9, in one embodiment, the pacemaker cord 32 may include a quick disconnect connector 330 providing a "D" shaped flange 332 mating with a corresponding "D" shaped receptacle of the corresponding pace generator connector 172 and supporting first and second prongs 334, i.e., positive and negative prongs, arranged in a lateral side-by-side configuration received within corresponding female-style terminals 313 of the pace generator connector. The "D" shaped flange 332 makes the mating orientation of the quick disconnect connector 330 of the pacemaker cord 32 easy to match with the pace generator connector 172. The quick disconnect connector 330 may further include a push button 336 associated with a slidable detent mating and un-mating with a corresponding hole or recess of the pace generator connector 172.

The quick disconnect connector 330 is further coupled to a Y connector 338 including a first cable 340 coupled to the quick disconnect connector 330 and branching into two cables 342, 344 with wire connector ends 346 at the distal ends of the two cables 342, 344 coupled to and compatible with the external pacemaker 24. The quick disconnect connector 330 and the wire connector ends 346 may further include strain relief bushing (not shown) in the form of a series of ridges where the quick disconnect connector 330 and wire connector ends 346 meet the cables 340, 342, 344. Therefore, the external pacemaker 24 is electrically coupled to the connector 100 by the pacemaker cord 32 which provides an electrical connection between the pace generator connector 172 and the circuit assembly 148.

With reference to FIGS. 2 and 4, the connector 100 further includes a tethered cover 276 configured to cover or otherwise protect one or more of the electrical connections of the stud connector 168 and/or the pace generator connector 172. The cover 276 includes a mount 280 (FIG. 4), a first end 284 coupled to the mount 280 by a first flexible arm portion 288, and a second end 292 coupled to the mount 280 by a second flexible arm portion 296. In other words, the cover 276 is a double-ended cover with the first end 284 opposite the second end 292. The mount 280 is seated within a channel 300 formed in the housing 108, and the mount 280 includes an aperture 304 (FIG. 4) through which a portion of the stud connector 168 is received. In other words, the cover 276 is secured within the channel 300 on the housing 108 by the stud connector 168 being secured to the housing 108.

The first end 284 of the cover 276 includes a protruding boss 308 that is configured to be received within the pace generator connector 172 (i.e., a female style connector). More specifically, the protruding boss 308 is received within an interior cavity 312 defined by the pace generator connector 172. The second end 292 of the cover 276 includes a plug 316 with an aperture 320 formed therein. The plug 316 is configured to cover the stud connector 168 (i.e., a male style connector). More specifically, the stud connector 168 is partially received within the aperture 320 formed in the plug 316. In the illustrated embodiment, the cover 276 is made of a flexible material (e.g., elastomeric material) that permits the first flexible arm portion 288 and the second flexible arm portion 296 to move (i.e., flex) with respect to the mount 280. As such, the first end 284 and the second end 292 are movable with respect to the mount 280.

With reference to FIGS. 2 and 3, the connector 100 further includes attachment portions 222 formed on the housing 108. In the illustrated embodiment, the attachment portions 22 are curved (i.e., in the shape of an arc). The user may attach a clip (e.g., an ID badge clip) or other suitable securing device to the attachment portions 222 such that the connector 100 can be secured to, for example, a patient gown, bed sheet, or other patient side material. In other words, the connector 100 does not have to be placed directly on the skin of the patient 14. In one embodiment, the pace generator connector 172 may be oriented at a rear end of the connector towards the patient's head while the pacing wires 28 are received by the connector 100 opposite the pace generator connector 172 at a front end of the connector 100 towards the patient's feet. The stud connector 168 is positioned on a top wall parallel to the patient's chest which is the natural plane for ECG leads placed on the patient's chest. The opposed buttons 112, 116 are oriented on left and right sides of the connector 100 on opposed surfaces of the housing 108 to provide an easy grip for the users' hands between the thumb and the index and middle fingers.

In operation, the connector 100 is interconnected to various medical devices 18, 24, and 28 in the medical system 10. Specifically, the connector 100 permits simultaneous and continuous interconnection of the pacing wires 28, the pacemaker 24, and the ECG monitor 18. In particular, the ECG leadwire 36 is coupled to the stud connector 168, and the pacemaker cord 32 is electrically coupled to the pace generator connector 170. In addition to coupling the ECG monitor 18 and the pacemaker 24 to the connector 100, the user may electrically couple the epicardial pacing wires 26 to the connector 100 according to the below description.

At first, the connector 100 is in a neutral state shown in FIG. 8A. In the neutral state, the shroud 104 is in the first, retracted position and the biasing member 224 biases the first and second buttons 112, 116 toward their respective blocking positions. With the buttons 112, 116 in the blocking position, the blocking portion 260 of the blocking arms 236 are positioned between the terminals 156, 160 and the apertures 184, 188. While in the blocking position, the blocking portion 260 prevents a pacing wire 26 from being inserted into and electrically coupled to the circuit assembly 148. As such, the blocking portion 260 of the buttons 112, 116 protects the terminals 156, 160. Also, with the shroud 104 in the retracted position, the overall size of the connector 100 is reduced.

With reference to FIG. 8B, to electrically couple the pacing wires 28 to the connector 100, the first button 112 and/or the second button 116 may be actuated. In the illustrated embodiment, the first button 112 can be actuated independently of the second button 116. Specifically, the first button 112 is depressed along the actuation axis 248 by a user force 324, for example with an index finger and middle finger holding the right sidewalls 140 and a thumb depressing the button 112, and the second button 116 is depressed along the actuation axis 248 by a user force 328, for example with the index finger and middle finger holding the left sidewall 140 and the thumb depressing the button 116. With the first and second buttons 112, 116 fully depressed, the buttons 112, 116 are in the non-blocking position. When in the non-blocking position, the windows 264 formed on the blocking portions 260 are aligned with the corresponding aperture 184, 188 on the housing 108 and the exterior aperture 132, 136 on the shroud 104. In other words, when the buttons 112, 116 are in the non-blocking position, the connector 100 is configured to receive the end rod 52 of the pacing wire 28 into one of the terminals 156, 160.

With reference to FIG. 8C, once the end rod 52 of the pacing wire 26 is inserted into the terminal 156, 160, the button 112, 116 may be released by the user. After releasing the buttons 112, 116, the biasing member 224 biases the button 112, 116 back towards the blocking position of FIG. 8A. However, with the end rod 52 inserted into the terminal 156, 160 the button 112, 116 is prevented from returning completely to the blocking position. Instead, the button 112, 116 is biased to the capturing position in which the end rod 52 of the pacing wire 28 is pinched (i.e., secured) between the circuit assembly 148, the window 264 of the button 112, 116, and the aperture 184, 188 on the housing 108. In other words, the biasing member 224 biases the button 112, 116 to the capturing position in which the end rod 52 is secured within the connector 100. As such, the pacing wires 28 are automatically secured within the connector 100 after the user releases the buttons 112, 116. In the blocking position the end rod 52 makes a secure electrical connection with the first terminal 156 and second terminal 160.

With reference to FIG. 8D, the shroud 104 may be moved into the extended position while or after the pacing wires 28 are secured to the connector 100. In the illustrated embodiment, the shroud 104 fully encloses the end rod 52 extending outward from the housing 108 when the shroud 104 is in the extended position. In one embodiment, at least a portion of the insulated wire portion 56 of the pacing wire 28 is received within the shroud 104 when the shroud 104 is in the extended position. The epicardial pacing wires 28 are fragile and it is undesirable to have the pacing wires 28 (especially the end rod 52) exposed to the surrounding environment. For example, the pacing wires 28 are susceptible to breaking or other physical damage when exposed to the environment surrounding the patient 14. Furthermore, if the end rod 52 of the pacing wire 28 is exposed, the end rod 52 susceptible to electrostatic shocks that effect proper pacing of the heart and corrector monitoring of the cardiac rhythm.

To disconnect the pacing wire 28 from the connector 100, the corresponding button 112, 116 is depressed to move the button 112, 116 back into the non-blocking position (FIG. 8B). While the button 112, 116 is in the non-blocking position, the end rod 52 of the pacing wire 28 is free to be removed from the terminal 156, 160 and the connector 100. The pacing wires 28 may be removed from the connector 100 with the shroud 104 in the extended position, the retracted position, or any position there between.

It is understood that a threshold level of force may allow the proximate end 48 of the pacing wires 28 to be removed from the connector 100 without the corresponding buttons 112, 116 being moved back into the nonblocking position (FIG. 8B) in emergency situations, for example, if the pacing wires 28 are yanked out of the connector 100 by the patient. The threshold level of force may be less than the threshold level of force needed to pull the distal end 40 of the pacing wires 28 out from the patient's heart 44.

It is understood that the shroud 104 may be labeled with fiducial labels indicating the proper connection of the positive and negative pacing wires 28, for example, the apertures for the epicardial terminals 156, 160 may be labeled with a plus (+) sign and minus (−) sign, respectively, to indicate where the positive 358 or negative 360 wires of the epicardial pacing wires 28 should be inserted. Other indicia, such as arrows, may also indicate the direction, i.e., along the first and second insertion axis 192, 196, to pull or push the shroud 104 with respect to the inner housing 108 to lock or unlock the shroud 104 between the first, retracted position (FIG. 8A) and a second, extended position (FIG. 8D). Arrows may also be used to indicate the location of the buttons 112, 116 on the sidewalls of the connector 100 which are actuated to insert the pacing wires 28.

The connector 100 obviates the time-consuming need to switch the connections to the epicardial pacing wires 28 and lowers any risk of misconnection.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference, which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context. When elements are indicated to be electrically connected, that connection may be direct or through an intervening conductive element.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What is claimed is:

1. An interface unit for epicardial pacemaking and telemetry monitoring comprising:
   an electrically insulating housing;
   first and second electrical terminals accessible through corresponding apertures in the housing and adapted to releasably receive first and second epicardial lead wires extending into an interior of the housing parallel to an insertion axis;
   a first electrical connector attached to the insulating housing to releasably receive a pacemaker connector at third and fourth electrical terminals;
   a second electrical connector attached to the insulating housing to receive a telemetry monitor connection at a fifth terminal;
   a circuit positioned within the housing, the circuit providing electrical communication between the second and third electrical terminals and between the first, fourth terminal and the fifth terminal; and an electrically insulating shroud coupled to the housing providing first and second apertures for receiving the first and second epicardial wires, respectively, therethrough and further permitting continuous connection of the first and second epicardial wires to the first and second electrical terminals, respectively, and movably coupled to the housing to move between
- a first position providing a first distance from the first and second apertures to the first and second terminals, respectively, wherein an extended length of the first and second epicardial wires is uncovered by the shroud in the first position; and
- a second position providing a second distance from the first and second apertures to the first and second terminals, respectively, wherein the second distance is longer than the first distance to cover the extended length of the first and second epicardial wires in the second position.

2. The interface unit of claim 1 wherein the shroud is movable with respect to the housing along the insertion axis.

3. The interface unit of claim 1 wherein the housing provides a front and rear opposed surface and wherein the apertures of the first and second terminals are on a front surface and the first electrical connector is on an opposed rear surface so that the first and second epicardial wires and the first electrical connector from the pacemaker connector may extend parallel to a common axis.

4. The interface unit of claim 1 wherein the housing further provides opposed upper and lower surfaces and wherein the second electrical connector is on the upper surface.

5. The interface unit of claim 1 further including buttons capturing the first and second epicardial lead wires.

6. The interface unit of claim 5 wherein the buttons are on a left and right opposed surfaces of the housing.

7. The interface unit of claim 6 wherein the buttons are biased by a spring along an actuation axis to capture the first and second epicardial lead wires.

8. An interface unit for epicardial pacemaking and telemetry monitoring comprising:
- an electrically insulating housing;
- first and second electrical terminals accessible through corresponding apertures in the housing and adapted to releasably receive first and second epicardial lead wires extending into an interior of the housing parallel to an insertion axis;
- a first electrical connector attached to the insulating housing to releasably receive a pacemaker connector at third and fourth electrical terminals;
- a second electrical connector attached to the insulating housing to receive a telemetry monitor connection at a fifth terminal;
- a circuit positioned within the housing, the circuit providing electrical communication between the second and third electrical terminals and between the first, fourth terminal and the fifth terminal;
- an electrically insulating shroud providing first and second apertures for receiving the first and second epicardial wires therethrough before the first and second epicardial wires are received by the first and second electrical terminals and movably attached to the housing to move between a first position proximate to the first and second terminals and a second position removed from the first and second terminals providing an insulating cover over the first and second epicardial wires extending outward from the first and second terminals; and
- buttons capturing the first and second epicardial lead wires wherein the buttons are on a left and right opposed surfaces of the housing wherein the buttons are biased by a spring along an actuation axis to capture the first and second epicardial lead wires wherein the buttons are opposed first and second buttons biased in opposite direction along the actuation axis by a shared spring.

9. The interface unit of claim 7 wherein the actuation axis is orthogonal to the insertion axis.

10. An interface unit for epicardial pacemaking and telemetry monitoring comprising:
- an electrically insulating housing;
- first and second electrical terminals accessible through corresponding apertures in the housing and adapted to releasably receive first and second epicardial lead wires extending into an interior of the housing parallel to an insertion axis;
- a first electrical connector attached to the insulating housing to releasably receive a pacemaker connector at third and fourth electrical terminals;
- a second electrical connector attached to the insulating housing to receive a telemetry monitor connection at a fifth terminal;
- a circuit positioned within the housing, the circuit providing electrical communication between the second and third electrical terminals and between the first, fourth terminal and the fifth terminal;
- an electrically insulating shroud providing first and second apertures for receiving the first and second epicardial wires therethrough before the first and second epicardial wires are received by the first and second electrical terminals and movably attached to the housing to move between a first position proximate to the first and second terminals and a second position removed from the first and second terminals providing an insulating cover over the first and second epicardial wires extending outward from the first and second terminals; and
- buttons capturing the first and second epicardial lead wires wherein the buttons are on a left and right opposed surfaces of the housing wherein the buttons provide a blocking arm extending into the housing and positioned between the first and second electrical terminals and the first and second apertures in a first position and provide a path between the first and second electrical terminals and the first and second apertures in a second position.

11. The interface unit of claim 10 wherein the blocking arm includes a window that is aligned along the insertion axis when the button is in the second position.

12. The interface unit of claim 1 wherein the circuit provides a resistance of at least 1 kilo-ohms.

13. The interface unit of claim 1 further comprising a tethered cover covering at least one of the first and second connectors.

14. The interface unit of claim 1 further comprising fiducial labels of minus and plus signs positioned proximate the first and second apertures respectively.

15. The interface unit of claim 1 further including a detent positioned between the housing and the shroud in at least one of the first and second positions.

16. The interface unit of claim 1 wherein the second electrical connector is a stud connector defined by a metallic boss extending outwardly from the housing and electrically coupled to the circuit assembly, wherein the stud connector is positioned on an exterior of the housing.

17. A connector assembly for epicardial pacemaking and telemetry monitoring comprising:
- a pace generator providing electrical impulses configured to provide electrical pacing to a heart of a patient through epicardial pacing leads connected to the heart;
- a telemetry monitor configured to receive electrical cardiac signals from the epicardial pacing leads to provide a display of the electrical cardiac signals; and
- an interface unit comprising:
  - an electrically insulating housing;
  - first and second electrical terminals accessible through corresponding apertures in the housing and adapted to releasably receive first and second epicardial lead wires extending into an interior of the housing parallel to an insertion axis;
  - a first electrical connector attached to the insulating housing to releasably receive a pacemaker connector at third and fourth electrical terminals;
  - a second electrical connector attached to the insulating housing to receive a telemetry monitor connection at a fifth terminal;
  - a circuit positioned within the housing, the circuit providing electrical communication between the second and third electrical terminals and between the first, fourth terminal and the fifth terminal; and
  - an electrically insulating shroud coupled to the housing providing a first and second apertures for receiving the first and second epicardial wires, respectively, therethrough and further permitting continuous connection of the first and second epicardial wires to the first and second electrical terminals, respectively, and movably coupled to the housing to move between
    - a first position providing a first distance from the first and second apertures to the first and second terminals, respectively, wherein an extended length of the first and second epicardial wires is uncovered by the shroud in the first position; and
    - a second position providing a second distance from the first and second apertures to the first and second terminals, respectively, wherein the second distance is longer than the first distance to cover the extended length of the first and second epicardial wires in the second position.

18. The assembly of claim 17 wherein the shroud is movable with respect to the housing along the insertion axis.

19. The assembly of claim 17 wherein the first aperture and first terminal are aligned along a first insertion axis and the second aperture and second terminal are aligned along a second insertion axis, and the first and second insertion axes are spaced apart in parallel.

20. The assembly of claim 17 further comprising buttons capturing the first and second epicardial lead wires.

* * * * *